United States Patent [19]

Bellin et al.

[11] Patent Number: 4,735,613
[45] Date of Patent: Apr. 5, 1988

[54] PRESSURE INFUSION DEVICE

[75] Inventors: Matthew E. Bellin, Burnsville; Joseph A. Marino, Jr., Apple Valley, both of Minn.

[73] Assignee: Biomedical Dynamics Corporation, Burnsville, Minn.

[21] Appl. No.: 922,173

[22] Filed: Oct. 23, 1986

[51] Int. Cl.$^4$ ............................................. A61M 5/00
[52] U.S. Cl. .................................... 604/141; 604/142; 604/118
[58] Field of Search ............... 604/118, 141, 142, 185, 604/186, 150; 222/94, 95; 73/146.2, 714, 715, 729, 731; 116/34 R; 137/69

[56] References Cited

U.S. PATENT DOCUMENTS

| | | | |
|---|---|---|---|
| 1,197,196 | 9/1916 | Folberth | 73/731 |
| 1,237,512 | 8/1917 | Harrison et al. | 73/146.2 |
| 1,806,372 | 5/1931 | Stille | 73/146.2 |
| 1,924,921 | 8/1933 | Frank | 116/34 R |
| 2,368,564 | 1/1945 | Pascoo | 73/146.2 |
| 2,618,977 | 11/1952 | Hottenroth | 116/34 R |
| 4,090,514 | 5/1978 | Hinck et al. | 604/142 |
| 4,507,116 | 3/1985 | Leibinsohn | 604/142 |
| 4,551,136 | 11/1985 | Mandl | 604/141 |

Primary Examiner—Dalton L. Truluck
Assistant Examiner—F. Wilkens
Attorney, Agent, or Firm—Kinney & Lange

[57] ABSTRACT

A pressure infusion device for medical applications for applying pressure to a sealed bag of liquid, such as an I.V. bag, in which the pressure gauge is fastened directly in the pressure applying bag which presses against the I.V. bag. The gauge has a movable plunger which moves outwardly from the bag by an amount depending upon the pressure within the bag. The pressure infusion arrangement is designed to be relatively inexpensive so that it can be discarded after being used. There are two forms, one in which the I.V. bag is held against the pressure applying bag by a mesh which is secured to a fabric to form a pocket for the I.V. bag and the pressure applying bag. In the other form, the mesh is secured directly to the edge of the pressure applying bag.

10 Claims, 3 Drawing Sheets

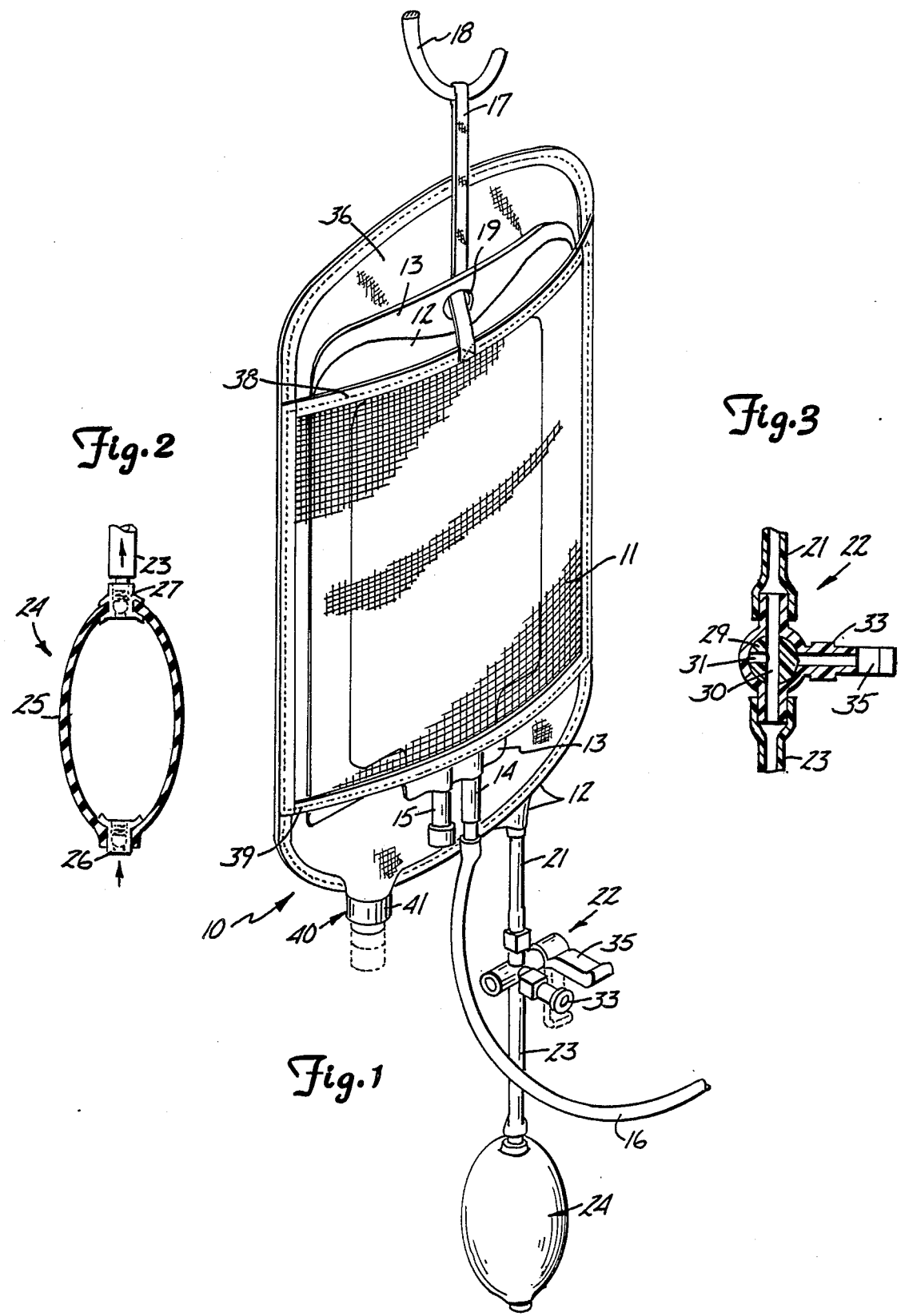

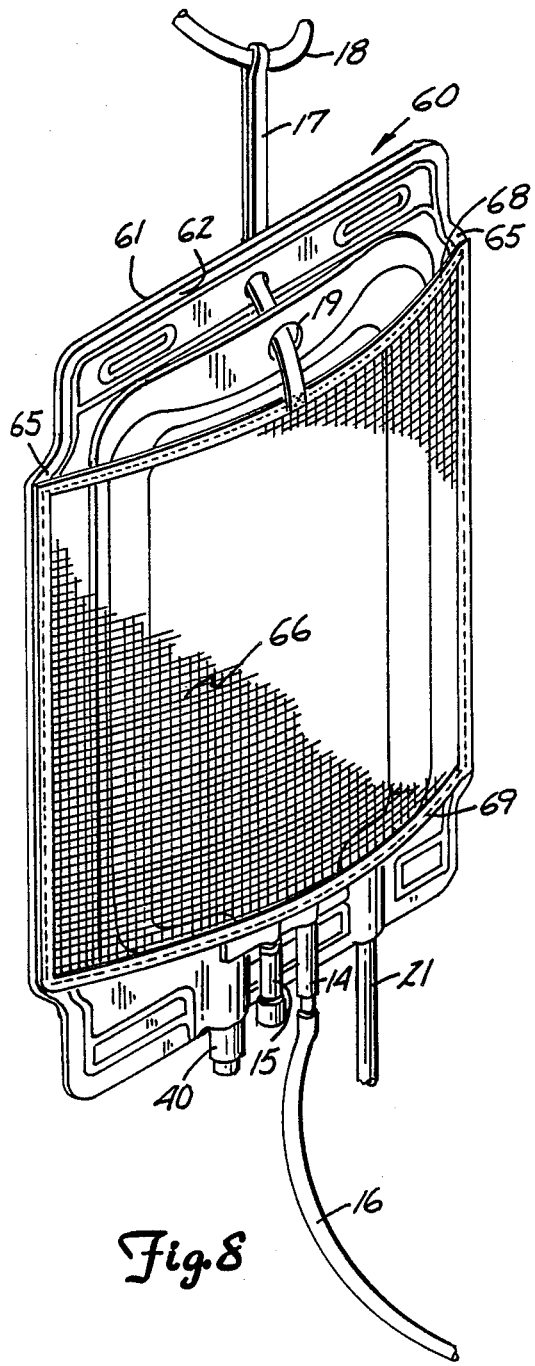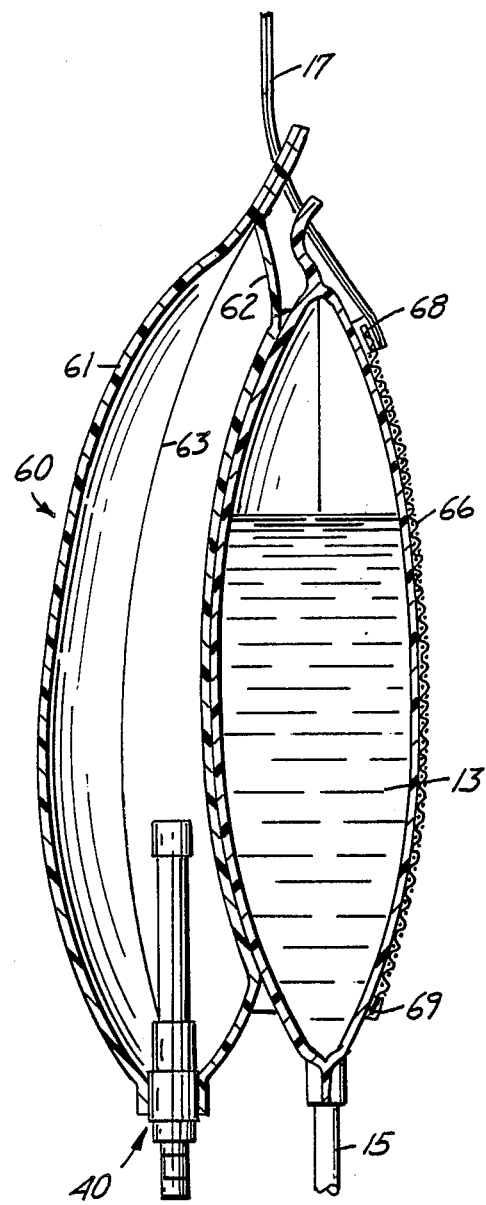

PRESSURE INFUSION DEVICE

BACKGROUND OF THE INVENTION

1. Field of the Invention.

The present invention relates to a pressure infusion device, particularly one with an improved gauge for measuring the pressure within a pressure chamber of such a pressure infusion device.

Various liquids for infusion into the body, such as a saline solution, whole blood and plasma, are normally supplied in disposable sterile sealed bags or receptacles of flexible plastic material having an outlet adapted to be punctured by a coupler connected to it, the liquid in the bag being supplied by a delivery tube to the desired region of the body. Such bags are commonly referred to as I.V. bags. In normal use, such as I.V. bag is suspended above the patient and the liquid is permitted to flow by gravity. Often, however, it is desired to speed up the delivery of liquid and in such a case, the bag of liquid is subjected to a source of pressure which maintains the liquid under pressure and speeds up the delivery of liquid. Another use for the application of pressure is to administer fluid to arteries where the pressure in the artery exceeds the pressure which can be generated by merely suspending a bag and relying upon the pressure of gravity. This has been commonly done by providing a second container in the from of a pressure bag which is held in engagement with the sealed bag to apply pressure thereto. The pressure is normally applied by pumping air into the pressure bag. In order to determine what pressure is being applied, it is customary to use a gauge connected to a tube connected to and projecting from the bag or a gauge which is connected to the tube extending between the pump and the bag. A typical gauge is a circular gauge having a movable pointer.

A typical device of the type just described is shown in the Hinck et al U.S. Pat. No. 4,090,514. In many instances, the bag for applying pressure to the sealed liquid bag is a bag which is of a permanent nature and which must be cleaned and sanitized after each use. The cost of cleaning and sanitizing such a bag is relatively substantial. Furthermore, these pressure applying devices are of limited life and are relatively expensive.

SUMMARY OF THE INVENTION

The present invention is concerned with a relatively inexpensive device for applying pressure to a liquid containing bag, such as an I.V. bag, the apparatus containing a pump and a pressure gauge, and in which the entire unit for applying pressure is sufficiently inexpensive that it can be discarded after having been used. Since the I.V. bag itself is always discarded after each use, it becomes unnecessary for any of the equipment involved to be cleaned and sanitized. As long as the apparatus for pressurizing the I.V. bag is relatively inexpensive, it is economically feasible to discard the bags after each use. This results in a substantial saving for the hospital or other medical facility administering such liquids.

The pressure infusion device of the present invention employs a sleeve secured to the pressure bag into which the I.V. or similar bag is slipped. As pressure is applied to the pressurizing bag, the I.V. bag is held firmly in position. This type of arrangement has already been proposed. The problem, however, with prior apparatus of this type is that the pressure gauge is a separate unit which is connected by tubing to the pressurizing bag, as previously stated. Such gauges are often relatively expensive and add substantially to the cost of the equipment. Normally it would not be economical to discard the gauge.

The present invention is concerned with such an arrangement in which a relatively simple pressure gauge is secured within the pressure bag itself in such a way that the pressure can be readily observed from all directions at all times. The provision of such a relatively inexpensive gauge secured to the bag itself makes it possible to produce a unit which economically can be thrown away after one use. This makes it possible, as discussed above, to discard all of the equipment after each use so as to eliminate the need for cleaning and sanitizing of any of the equipment involved.

The gauge used is of a type in which there is a cylindrical member extending through a lower wall within the pressurizing bag. Preferably, a rolling diaphragm is employed between the plunger and the tube to provide a seal which permits movement of the plunger within the tube. The diaphragm may merely extend over the top of the plunger so that it is unnecessary to provide any connection between the diaphragm and the plunger.

Pressure in the pressurizing bag can be applied by a bulb pump of the type conventionally used for pumping a pressurizing bag or a blood pressure measuring cuff. Such a bulb pump has a series of check valves to permit air to flow toward the bag, but prevent it from escaping. Suitable means are provided for releasing the pressure in the bag.

Further features of the invention will be apparent from a consideration of the accompanying specification, claims and drawing.

BRIEF DESCRIPTION OF THE DRAWINGS

FIG. 1 is a perspective view of the improved pressure infusion device showing the device of the present invention in which is disposed a conventional I.V. bag;

FIG. 2 is a cross-sectional view of the pump used for introducing pressure into the pressure bag;

FIG. 3 is a sectional view of a valve selectively positionable to either admit pressure to the pressure bag or to release pressure from the bag;

FIG. 8 is a perspective view of a modified form of the pressure bag; and

FIG. 9 is a longitudinal sectional view of the bag of FIG. 8.

DETAILED DESCRIPTION OF THE PREFERRED EMBODIMENTS

Figure 4:
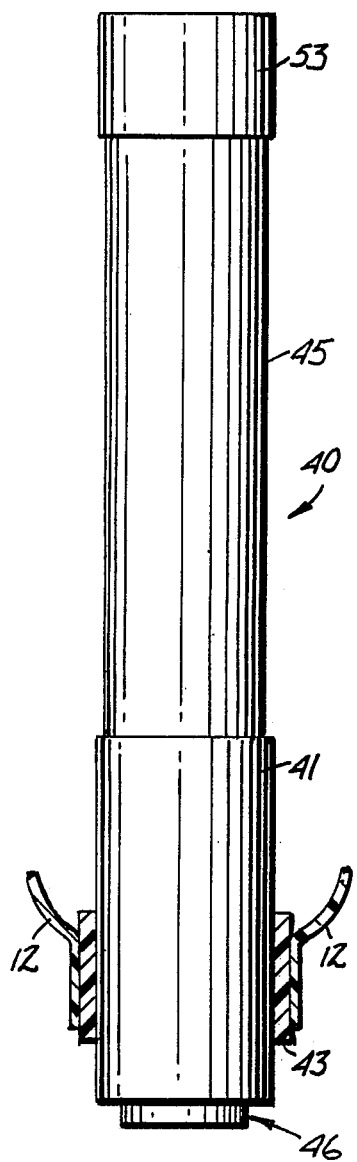
FIG. 4 is an elevational view of the novel gauge used with the improved pressure infusion device, the gauge being shown in the position in which very little pressure is in the pressure bag.

Referring first to FIG. 1, the improved infusion device is shown in perspective. A liquid containing bag is indicated with a reference numeral 13. The bag is of conventional construction being formed of plastic material. At the bottom of the bag there are two tubes 14 and 15. The tube 14 is connected to a tube 16 leading to a point of application to the body. The tube 16 may be connected to a needle which is inserted into a vein for introducing the fluid within the bag 13 into the vein. The second tube 15 is a tube which is used for introducing various medicines into the liquid within the bag 13. The bag just described is a typical I.V. bag commonly used in hospitals and other medical establishments.

Pressure bag 12 is held against the I.V. bag 13 in a manner which will be presently described. This bag is a closed bag preferably formed of two sheets of plastic material which are fastened together along their edges. An inlet tube 21 is secured to the bottom of the bag and is used for introducing air into the bag under pressure. The tube 21 is connected through a valve 22 and a second tube 23 to a bulb pump 24 shown in section in FIG. 2. This bulb is of a conventional type used for pumping air into a chamber. One common use is in connection with blood pressure measuring cuffs. As will be clear from FIG. 2, the bulb pump 24 consists of a bulb 25 having an inlet valve 26 which is biased downwardly to closed position. There is also an outlet valve 27 likewise biased downwardly to closed position. When the bulb 25 is squeezed, air within the bulb is forced past the outlet valve 27 into the tube 23. When the bulb is released, the valve 27 closes and air is drawn in through the valve 26 against its bias. It is obvious that by repeated operation of the bulb 25, air can be introduced into the pressure bag 12 to inflate it and thus exert pressure against the I.V. bag 13. The valve 22 is shown in section in FIG. 3. There is a handle 35 which is shown in the position in which air can flow from tube 23 to tube 21 and hence into the pressure bag 12. The valve 22 has a rotatable valve stem 29 which is movable to either of two positions 90° disposed from each other. There is a passage 30 extending through the valve stem 29 and when in the position shown in section in FIG. 3, in which the handle 35 is in the position shown in FIG. 1, air can pass freely from the bulb pump 24 through the conduits 23 and 21 into the bag. There is a side passage 31 communicating with the passage 30. If the valve stem 29 is rotated 90° in a clockwise direction as viewed in FIG. 3, air can now flow from tube 21 through the side passage 31 and the main passage 30 out through a bleed passage 33. At the same time, passage of air between tubes 21 and 23 is blocked because the passage 30 is now at right angles to that shown in FIG. 3 and there is no communication through passage 30 between tubes 21 and 23. In the position just described, the pressure can bleed off through the bleed 33. Again, such valves are old and well known, and are used for relieving pressure in a pressure chamber.

The I.V. bag 13 and the pressure bag 12 are held in engagement with each other by a fabric mesh 11 which is secured at its opposite sides to a fabric sheet 36. The fabric mesh 11 along with the fabric sheet 36 thus form a pocket into which the air pressure bag 12 and the I.V. bag 13 can be inserted and held in engagement with each other. The fabric mesh 11 has binding strips 38 and 39 at the top and bottom. Secured to the binding strip 38 is a strap 17 which can be passed through an opening 19 on the edge of the I.V. bag 13 and then placed over a hook 18 of a typical I.V. stand. The pressure bag 12 and the I.V. bag 13 are thus both supported from the hook 18.

A pressure gauge 40 extends through the bottom of the pressure bag 12 and is secured thereto. It is this pressure gauge that is a very important feature of our invention. It provides an inexpensive pressure gauge which, because it is fastened directly to the pressure bag, leads to an economy in manufacture. Furthermore, as will be pointed out, the pressure gauge provides a readily visible indication of the pressure from all directions to someone pumping up the bag 12.

The details of the pressure gauge 40 are shown in FIGS. 4, 5, 6 and 7. The pressure gauge has an outer tube 43 which is secured to the wall of the pressure bag 12 as best shown in FIGS. 4 through 7. The short tube 43 is preferably sealed between the two sheets used to form the bag 12. Secured within the tube 43 is a further tube 41. The tube 41 is secured within the short tube 43 by cement or by some similar means. The tube 41 has a reduced upper portion 45, there being a flange 44 between the lower portion 41 and the upper portion 45. Located within the tube 41 is a plunger 46, best shown in FIG. 5. This plunger has an upstanding stem 47 terminating in a nipple portion 50 connected to the stem by a frustoconical portion 51. A disk 48 is secured between the conical portion 41 and a flange 52 at the top of the lower portion of stem 47. The disk 48 provides a stop for one end of a spring 54 interposed between the disk 48 and the inwardly extending flange 44 of the housing 41. The spring 54 thus biases the cylinder 46 upwardly to the position shown in FIGS. 4 and 5.

A rolling diaphragm 52 extends over the upper end of the nipple 50 and downwardly along the frustoconical portion 51. The upper end portion 53 of the rolling diaphragm 52 is brought up over the top of the tube 45 and stretched over to form a seal between the outer end 53 of the diaphragm and the tube 45.

Figure 7:
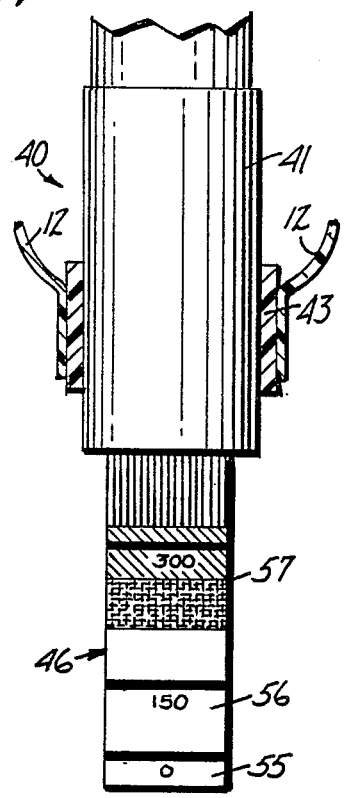
FIG. 7 is a view similar to FIG. 6, but with the plunger extending further outwardly indicating a higher pressure within the pressure bag.
Figure 6:
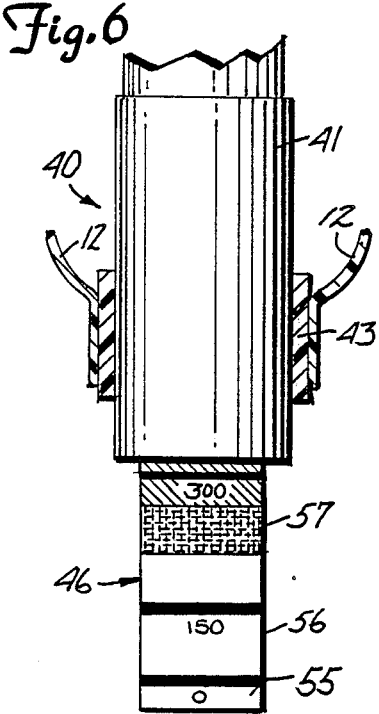
FIG. 6 is a view of the lower portion of the gauge of FIG. 4 with a pressure indicating plunger standing a part of the way out of the gauge.
Figure 5:
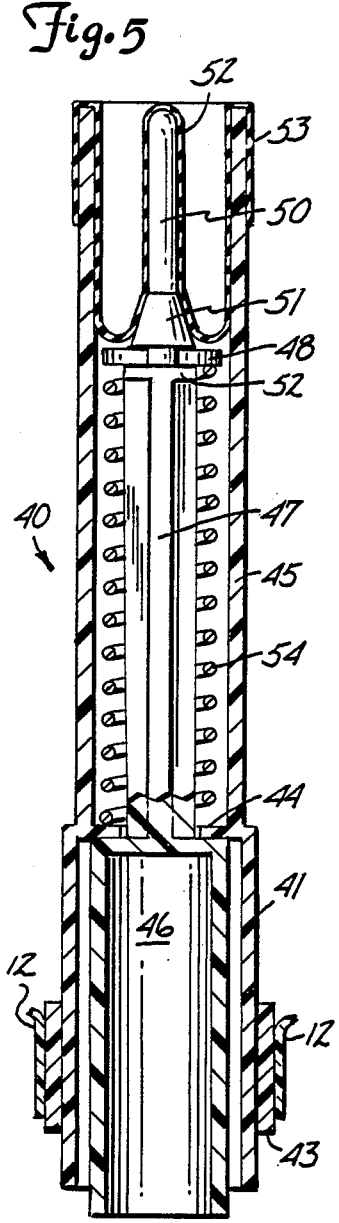
FIG. 5 is a longitudinal sectional view of the gauge of FIG. 4.

It would be readily apparent that if sufficient pressure is applied to the upper end of the rolling diaphragm 52, the whole plunger assembly 46 will be forced downwardly so that the lower end of the plunger 46 will project out of the tube 41. This is shown in FIGS. 6 and 7. The lower end of the plunger is colored with various bands 55, 56 and 57, and numerals are applied indicating the pressure in millimeters of mercury. Thus, in FIG. 6, the pressure is slightly over 300 millimeters of mercury. In FIG. 7, the pressure is substantially over 300 millimeters of mercury.

The pressure gauge 40 of the present invention provides an extremely inexpensive and very visible manner of indicating the pressure. As distinguished from a round gauge which is secured to a tube leading to the pressure bag, the pressure gauge 40 is always adjacent to the pressure bag 12 and the extent to which the plunger 46 extends out of the bag is likewise readily visible to anyone operating the pump. Furthermore, the cost of securing such a pressure gauge to the bag is substantially less than where the gauge is inserted into tubing leading to the bag.

Because of the simplicity of the gauge 40, and the manner in which it is secured to the pressure bag 12, it becomes possible to produce a pressure infuser at a sufficiently low cost that it can be discarded after each use at a cost less than the cost of sanitizing plus the depreciation of a more elaborate bag. As explained above, the pressure applying units now in use are sterilized after each use and can only be used a limited number of times before they must be discarded. With the arrangement of the present invention, the entire pressure applying device along with the I.V. bag can be discarded after it has been used.

MODIFICATION OF FIGS. 8 AND 9

The modification of FIGS. 8 and 9 is very similar to that of the device just described. The primary difference is that the fabric mesh which engages the liquid containing or I.V. bag is fastened directly to the pressure bag rather than to a separate fabric member such as member 36 of FIG. 1. In order to enable a comparison of the figures, elements which are identical to elements in FIGS. 1 through 7 have been given the same reference numerals. Thus, the I.V. bag is designated by reference numeral 13, the gauge by the reference numeral 40, and so forth.

In this Figure, the pressure bag is indicated by the reference numeral 60. As is clear from the cross-sectional view of FIG. 9, there are two sheets 61 and 62 which are joined together along a seam line 63 against the gauge 40. The sheets can be of flexible plastic material and heat sealed together. The sheets 61 and 62 are so formed as to leave flanges 65 along their outer edges. The mesh fabric in this embodiment is indicated by reference numeral 66. This fabric is fastened to the flanges 65. The mesh fabric has bindings 68 and 69 at the top and bottom, and the strap 17 which hooks over the hook 18 of the I.V. stand and is secured to the binding 68. The sheets 61 and 62 may be formed of a suitable thin polyurethane.

The arrangement of FIGS. 8 and 9 is thus somewhat simpler than that of the other figures in that the fabric 66 is fastened directly to the pressure bag so that there is no need of a further fabric layer to which the mesh fabric is secured. The arrangement of FIGS. 8 and 9 is thus even less expensive than that of FIGS. 1 through 7, and makes it even more economically possible to discard the entire unit after each use.

CONCLUSION

It will be readily apparent that the present invention provides for a very inexpensive type of infusion device which can be discarded after being used. The invention embodies a unique type of gauge for this type of application, the gauge being sealed to the pressure bag of the infusion device and having a portion projecting outwardly so as to clearly indicate the pressure within the bag.

While we have described certain embodiments for the purpose of illustration, it should be understood that our invention is limited solely by the scope of the appended claims.

What is claimed is:

1. A pressure infusion device for medical applications comprising:
   a sealed bag of flexible material having means secured thereto for holding a liquid containing plastic bag to apply pressure to the liquid containing bag as fluid under pressure is introduced into the sealed bag, the liquid containing bag having an outlet connected to a tube for delivering the liquid in the bag to a medical patient;
   means for introducing fluid under pressure into the sealed bag; and
   a gauge for measuring the pressure within the sealed bag, the gauge being in the form of a tube extending through a wall of the sealed bag and comprising a plunger movable in the tube and biased into the sealed bag, said plunger being exposed to the pressure within the sealed bag, the plunger movable outwardly against its bias to an extent dependent upon the pressure in the sealed bag, the plunger projecting out of the tube when it moves outwardly and having indicia thereon to indicate the extent to which the plunger has moved outwardly.

2. The pressure infusion device of claim 1 in which the means for holding the liquid containing plastic bag against the sealed bag is a flexible fabric of a length approximately that of the liquid containing bag and which has at least two opposite side edges, said opposite side edges being fastened to the sealed bag so that the liquid containing bag can be inserted between the fabric and the sealed bag while the latter has no pressure applied thereto.

3. The pressure infusion device of claim 2 in which the fabric is a mesh fabric having top and bottom edges, said fabric being reinforced along said top and bottom edges.

4. The pressure infusion device of claim 1 in which the indicia on the lower end of the plunger is in the form of a plurality of bands of color, each band being of a different color.

5. The pressure infusion device of claim 1 in which the means for introducing fluid under pressure into the sealed bag includes a bulb and check valve means for pumping air into the sealed bag.

6. The pressure infusion device of claim 1 in which means are provided for releasing the pressure in the sealed bag.

7. The pressure infusion device of claim 1 in which a seal between the tube and the plunger is formed by a rolling diaphragm secured at its outer edge in a fluid tight manner to the tube.

8. The pressure infusion device of claim 7 in which the rolling diaphragm extends over the top of the plunger.

9. The pressure infusion device of claim 1 in which the tube of the gauge is sealed within an outer tube which extends through and is sealed to the lower wall of the bag.

10. The pressure infusion device of claim 1 in which the sealed bag is formed of two sheets of flexible plastic material which is heat sensitive, the sheets being heat sealed together adjacent their outer edges and around the tube of the gauge.

* * * * *